United States Patent [19]

Shibusawa et al.

[11] Patent Number: 5,035,895

[45] Date of Patent: Jul. 30, 1991

[54] EMULSIFIED AND SOLUBILIZED PHARMACEUTICAL PREPARATION

[75] Inventors: Koichi Shibusawa, Gunma; Shigemitsu Ohsawa, Saitama, both of Japan

[73] Assignee: Eisai Co., Ltd., Tokyo, Japan

[21] Appl. No.: 300,407

[22] Filed: Jan. 20, 1989

[30] Foreign Application Priority Data

Jan. 22, 1988 [JP] Japan .................................. 63-12063

[51] Int. Cl.$^5$ ............................................. A61K 37/22
[52] U.S. Cl. .................... 424/450; 424/422; 426/656; 426/662
[58] Field of Search .................... 424/450, 1.1, 9, 490, 424/422; 264/4.3; 426/656, 662

[56] References Cited

U.S. PATENT DOCUMENTS

| | | | |
|---|---|---|---|
| 3,962,416 | 6/1976 | Katzen | 424/493 |
| 4,568,667 | 2/1986 | Shirakawa et al. | 514/53 |
| 4,743,449 | 5/1988 | Yoshida et al. | 424/420 |
| 4,744,989 | 5/1988 | Payne et al. | 424/490 |
| 4,751,241 | 6/1988 | Motoyama et al. | 514/937 |
| 4,830,858 | 5/1989 | Payne et al. | 424/450 |

FOREIGN PATENT DOCUMENTS

| | | |
|---|---|---|
| 0132821 | 2/1985 | European Pat. Off. . |
| 0144434 | 6/1985 | European Pat. Off. . |
| 0214501 | 3/1987 | European Pat. Off. . |

Primary Examiner—Thurman Page
Attorney, Agent, or Firm—Flynn, Thiel, Boutell & Tanis

[57] ABSTRACT

An aqueous solution comprises a fat-soluble substance, a phosphatide, a polyhydric alcohol and a basic amino acid, a salt thereof or Meglumin. It is uniformly emulsified and solubilized for the pharmaceutical use.

8 Claims, 1 Drawing Sheet

EMULSIFIED AND SOLUBILIZED PHARMACEUTICAL PREPARATION

The invention relates to an aqueous solution of a fat-soluble substance, for example, a fat-soluble vitamin, and then provides a solution, uniformly emulsified or solubilized, which is obtained even with mild stirring.

In the prior art, an aqueous solution of a fat-soluble substance, a phosphatide and a polyhydric alcohol is obtained with use of a high pressure homogenizer or a ultrasonic emulsifying machine for a long time such as 60 minutes. A strong dispersing power is needed. This is a reason why mass-production cannot be conducted.

SUMMARY OF THE INVENTION

In the invention, instead of such a machine, a stirring machine having a mild stirring action, for example Polytron (tradename) and a homomixer, is available to offer a mild shearing stress. Alternatively a ultra-sonic emulsifying machine can be used, however, for a short time. This can be advantageously attained with incorporation of a basic amino acid, a salt thereof or Meglumine (N-methylglucamine) into the solution. The invention provides an aqueous solution which comprises a fat-soluble substance, a phosphatide, a polyhydric alcohol and a basic amino acid, a salt thereof or Meglumine.

It is preferable that the solution comprises the fat-soluble substance, the phosphatide, the polyhydric alcohol, each in a conventional amount, and then 0.1 to 0.5 part by weight, based on 1 part of the phosphatide, of the basic amino acid, a salt thereof and Meglumine.

It is also preferred that the basic amino acid is L-arginine or L-lysine, the fat-soluble substance is selected from vitamin E, vitamin E acetate, coenzyme Q10, vitamin A, an aliphatic ester of vitamin C, gamma-linolenic acid and vegetable oils, the phosphatide is soy bean lecithin or egg yolk lecithin, and the polyhydric alcohol is glycerin or D-sorbitol.

The invention provides the pharmaceutical use of the solution as defined above as an injection liquid, an emulsion or an oral liquid preparation.

WORKING EXAMPLE

EXAMPLE 1

Figure 1:
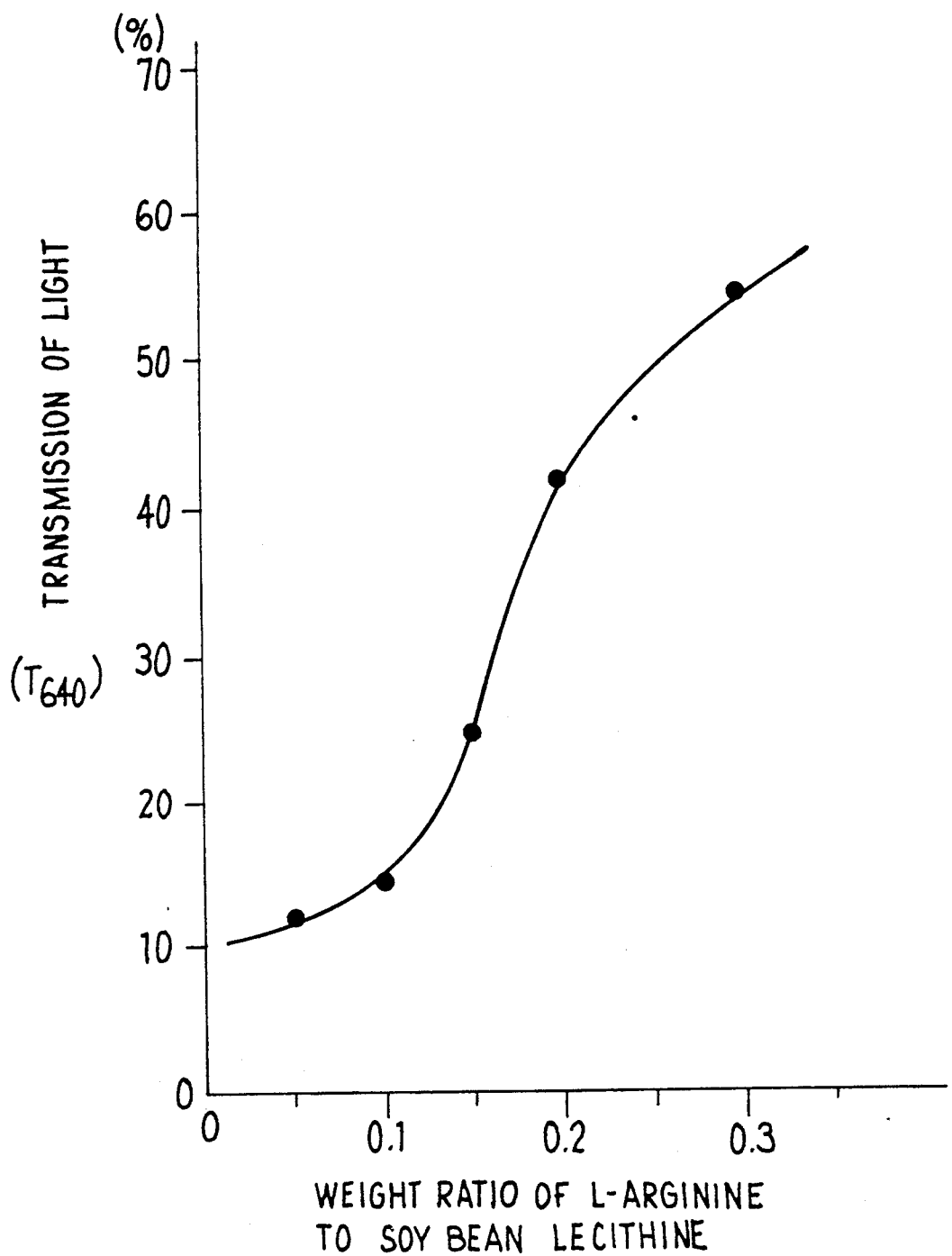
FIG. 1 shows results of Test III.

An aqueous solution was prepared in the following way. A solution A comprising 100 mg of vitamin E acetate, 30 mg of L-arginine, 100 mg of purified soy bean lecithin and 770 mg of glycerin was prepared with Polytron. One gram of the solution A was mixed with 12 ml of purified water, while being stirred. A mixture B comprising 0.5 ml of ginseng extract liquid, 25 mg of nicotinic amide, 10 mg of FMN(VB2), 50 mg of caffein, 3000 mg of D-sorbitol, 5000 mg of purified white sugar, 18 mg of benzoic acid, 20 mg of dl-malic acid and a suitable amount of sodium citrate was dissolved in 12 ml of purified water. A mixture D comprising 3 mg of ethyl paraben, 1 ml of ethanol and a trace of a perfume was added to and mixed with the solution B. The solutions A and B were mixed with each other and the mixture was adjusted with sodium citrate to have a pH of 5.5. Then further purified water was added thereto to a total volume of 30 ml. The finish liquid was found to be transparent and clear.

EXAMPLE 2

A mixture B comprising 0.3 g of Meglumine, 6.9 g of glycerin and 0.8 ml of ethanol was heated to obtain a solution. A mixture A comprising 1.0 g of soy bean oil and 1.0 g of soy bean phosphatide was added to the solution B. A clear solution was obtained with use of Polytron.

EXAMPLE 3

3 mg of Meglumine was dissolved in a mixture of 27 mg of glycerin and 50 mg of a 70% solution of D-sorbitol. 10 mg of coenzyme Q and 10 mg of purified egg yolk lecithin were added to the solution. The mixture was treated with Polytron to prepare an aqueous solution. The solution was further diluted with water and adjusted with a suitable amount of a solution of citric acid in purified water for injection to have a pH of about 7 and thereby obtain 1 ml of a clear injection liquid.

TEST I

The aqueous solutions listed in Table 1 were prepared and examined for water dispersibility. The components 1 and 4 were dissolved in water, while being heated. Then the components 2 and 3 were added to the solution. The mixture was treated with Polytron at 7000 revolution per minute (rpm) for 30 minutes. The obtained solutions were observed with respect to their appearance. A 3 percent dispersion of each solution in water was obtained and it was observed. Moreover it was measured to determine its transmittance of light at O.D. 640 nm.

TABLE 1

|  | composition | | |
| --- | --- | --- | --- |
|  | 1 | 2 | 3 |
| component |  |  |  |
| 1 L-arginine | — | 0.3 g | — |
| Meglumine | — | — | 0.3 g |
| 2 soy bean lecithin | 1.0 g | 1.0 g | 1.0 g |
| 3 vitamin E acetate | 1.0 g | 1.0 g | 1.0 g |
| 4 glycerin | 8.0 g | 7.7 g | 7.7 g |
| appearance | milky | clear | clear |
| dispersibility in water | milky | clear | clear |
| transmittance at 640 nm | separates | over 30% | over 20% |

The composition 1 is a control and the compositions 2 and 3 fall within the invention. The composition 1 was found to have oil and lecithin drops floating thereon.

TEST II

Aqueous solutions were prepared, as listed in Table 2, with various amounts of L-arginine. They were tested in for water dispersibility. The results are shown in Table 2. L-arginine was dissolved in glycerin with heating. Then soy bean lecithin and vitamin E acetate were added to the solution and the mixture was treated with Polytron at 7000 revolution per minutes for 30 minutes. They were observed in appearance. A 3% aqueous solution of each resultant composition was measured to determine its transmittance of light at O.D. 640 nm.

TABLE 2

| composition | 0/10 | 0.5/10 | 1/10 | 2/10 | 3/10 | 5/10 |
| --- | --- | --- | --- | --- | --- | --- |
| L-arginine | 0 | 0.05 | 0.1 | 0.2 | 0.3 | 0.5 |
| soy bean lecithin | 1 | 1 | 1 | 1 | 1 | 1 |

TABLE 2-continued

| | | | | | | |
|---|---|---|---|---|---|---|
| vitamin E acetate | 1 | 1 | 1 | 1 | 1 | 1 |
| glycerin | 8 | 7.95 | 7.9 | 7.8 | 7.7 | 7.5 |
| appearance | milky | clear | clear | clear | clear | clear |
| transmittance at 640 nm (%) | — | 10 | 15 | 20 | 30 | 40 |

Ratios in the uppermost column show those of L-arginine to lecithin. In the test on 0/10 in transmittance, some oil was found to separate out.

TEST III

Aqueous solutions were prepared with change of the amounts of L-arginine to soy bean lecithin. L-arginine was dissolved, while heated, in glycerin. Soy bean lecithin and vitamin E acetate were then added to the solution and the mixture was stirred with an ultra-sonic emulsifying machine for 90 seconds. The obtained aqueous liquids had a concentration of 3 percent by weight. They were measured to determine their light transparency at O.D. 640 nm. Results are shown in FIG. 1. The addition of L-arginine was found to be advantageous in comparison with no addition.

We claim:

1. A transparent, clear aqueous preparation consisting essentially of a fat-soluble substance selected from the group consisting of vitamin E, vitamin E acetate, coenzyme Q10, vitamin A, an aliphatic ester of vitamin C, gamma-linolenic acid and vegetable oils, said fat-soluble substance being emulsified or solubilized in the aqueous phase in the presence of a phosphatide, a polyhydric alcohol and a compound selected from the group consisting of basic amino acids, salts of basic amino acids and N-methylglucamine, the amount of said compound being from 0.1 to 0.5 parts by weight, per one part by weight of said phosphatide.

2. A transparent, clear, aqueous preparation consisting essentially of a fat-soluble substance selected from the group consisting of vitamin E, vitamin E acetate, coenzyme Q10, vitamin A, an aliphatic ester of vitamin C, gamma-linolenic acid and vegetable oils, said fat-soluble substance being emulsified or solubilized in the aqueous phase in the presence of a phosphatide selected from the group consisting of soy bean lecithin and egg yolk lecithin, a polyhydric alcohol selected from the group consisting of glycerin and D-sorbitol and a compound selected from the group consisting of L-lysine and L-arginine, the amount of said compound being from 0.1 to 0.5 parts by weight, per one part by weight of said phosphatide, said material being effective to solublize said fat-soluble substance and said phosphatide, said preparation having a transmittance of light at 640 nm of at least 15%.

3. A preparation as claimed in claim 1, in which said compound is L-arginine.

4. A preparation as claimed in claim 1, in which said phosphatide is soy bean lecithin or egg yolk lecithin.

5. A preparation as claimed in claim 1, in which said polyhydric alcohol is glycerin or D-sorbitol.

6. A transparent, clear, aqueous preparation consisting essentially of a fat-soluble substance selected from the group consisting of vitamin E, vitamin E acetate, coenzyme Q10, vitamin A, an aliphatic ester of vitamin C, gamma-linolenic acid and vegetable oils, said fat-soluble substance being emulsified or solubilized in the aqueous phase in the presence of N-methylglucamine, a phosphatide selected from the group consisting of soy bean lecithin and egg yolk lecithin, and a polyhydric alcohol selected from the group consisting of glycerin and D-sorbitol, the amount of said N-methylglucamine being from 0.1 to 0.5 parts by weight, per one part by weight of said phosphatide, said N-methylglucamine being effective to solubilize said fat-soluble substance and said phosphatide, said preparation having a transmittance of light at 640 nm of at least 15%.

7. A preparation as claimed in claim 1, wherein said compound is selected from the group consisting of L-arginine, L-lysine and a salt thereof.

8. A preparation as claimed in claim 1, wherein said compound is N-methylglucamine.

* * * * *